United States Patent [19]
Stepan

[11] Patent Number: 5,796,461
[45] Date of Patent: Aug. 18, 1998

[54] PROTECTIVE EYEGLASS ASSEMBLY

[75] Inventor: Walter Stepan, Lincoln, R.I.

[73] Assignee: Uvex Safety, Inc., Smithfield, R.I.

[21] Appl. No.: 635,204

[22] Filed: Nov. 22, 1995

[51] Int. Cl.⁶ .............................. G02C 1/04; G02C 1/00; G02C 5/20; G02C 5/14
[52] U.S. Cl. ..................... 351/106; 351/41; 351/86; 351/118; 351/120
[58] Field of Search .................................. 351/41, 44, 83, 351/86, 87, 104, 105, 106, 116, 118, 120, 130, 131; 2/440, 441, 442, 448, 449, 450

[56] References Cited

U.S. PATENT DOCUMENTS

| | | | |
|---|---|---|---|
| 4,405,212 | 9/1983 | Cooper | 351/83 |
| 5,530,490 | 6/1996 | Canavan | 351/106 |
| 5,555,037 | 9/1996 | Canavan | 351/118 |

*Primary Examiner*—Huy Mai
*Attorney, Agent, or Firm*—Salter & Michaelson

[57] ABSTRACT

A protective eyeglass assembly includes a frame having left and right lens frame portions, lens receiving apertures in the frame portions, a central bridge portion connecting the frame portions, and left and right temple bars. The eyeglass assembly further includes an integrally formed lens piece which is adapted to be detachably secured to the frame so that a user can interchange the frame and/or replace the lens piece. The lens piece includes left and right lens panels, a central bridge portion connecting the lens panels, left and right side shields, and left and right upper shields. The lens piece is received in assembled relation with the frame with the left and right lens panels aligned in registry with the left and right lens frame portions. The lens panels and bridge portion of the lens piece have an outer peripheral margin which is substantially similar to the left and right frame portions and bridge portion of the frame such that the lens piece is substantially hidden when viewing the eyeglass assembly from a frontal viewing position. The left and right lens panels further include stepped lens formations which are received in interfitting engagement into the lens receiving apertures of the frame when the lens piece is assembled with the frame. The temple bars are angularly adjustable with respect to the frame portion, and are further telescopically adjustable in length.

24 Claims, 5 Drawing Sheets

PROTECTIVE EYEGLASS ASSEMBLY

BACKGROUND AND SUMMARY OF THE INVENTION

The instant invention relates to protective eyewear, and more particularly to a protective eyeglass assembly including a frame portion and a protective lens piece which may be readily assembled and disassembled with the frame for quick, and efficient interchange of the frame and/or replacement of the lens piece.

The importance of wearing safety or protective glasses in many industrial environments is widely recognized, and as a result, a variety of different types and styles of protective eyeglasses have been heretofore available. While the currently existing protective eyeglasses are adequate for their intended purpose, there is nevertheless a continuing need for improved versions of protective eyeglasses. In this regard, protective eyeglasses which mimic current designer frame styles and which offer versatility to change frame colors or styles, and to replace lens pieces are believed to be highly desirable in the market.

The instant invention provides a novel and effective protective eyeglass assembly which has a high degree of versatility. More specifically, the eyeglass assembly of the instant invention comprises a frame, and a lens piece which is adapted to be detachably secured to the frame so that a user can interchange the frame for another frame of the same type, but of a different color or appearance, and/or replace the lens piece if the lens piece becomes damaged.

The frame comprises left and right lens frame portions, left and right lens receiving apertures respectively formed in the left and right lens frame portions, a bridge portion connecting the left and right lens frame portions, and left and right temple bars extending rearwardly from the left and right lens frame portions. The temple bars are angularly adjustable with respect to the left and right lens frame portions, and are also telescopically adjustable in length.

The lens piece is preferably integrally molded from a durable, transparent, plastic material and includes left and right lens panels, a central bridge portion connecting the left and right lens panels, left and right side shields extending rearwardly from left and right side extremities of the left and right lens panels, and left and right upper shields extending between left and right upper extremity portions of the left and right lens panels, and the left and right side shields, respectively.

The lens piece is received in assembled relation with the frame with the left and right lens panels aligned in registry with the left and right lens frame portions. The lens piece and the frame are secured in assembled relation by means of interengaging formations on the frame and lens piece. More specifically, the left and right temple bars each include an inwardly extending, horizontally disposed T-shaped pin, while the left and right side shields of the lens piece include a complementary vertically disposed slot for receiving their respective pins. The central bridge portion of the lens piece further includes a detent, while the bridge portion of the frame includes a small recess for receiving the detent. To assemble the frame and lens piece, the temple bars of the frame are bent outwardly to insert the pins into the slots in the side shields of the lens piece. In this regard, the lens piece is originally positioned with the lens panels facing downwardly so that the slots in the side shields are disposed horizontally and aligned with the pins, and then the lens piece is rotated forwardly and upwardly with respect to the frame to engage the lens piece detent with the recess in the bridge portion of the frame. The pins along with the detent cooperate to maintain the lens piece in assembled relation with the frame.

The left and right lens panels and the bridge portion of the lens piece are preferably formed with an outer peripheral margin which is generally similar to the outer peripheral margin of the left and right lens frame portions and the bridge portion of the frame such that the lens piece is substantially hidden from view when viewing the assembled eyeglasses from a frontal viewing position. Still further, the left and right lens panels each include a stepped lens formation which is received in interfitting engagement into the aligned lens receiving aperture of the frame portion when the lens piece is assembled with the frame. The stepped lens formation creates the perception that there are individual lenses snapped into the lens frame apertures.

It has been found that the protective eyeglass assembly of the instant invention has significant marketing advantages over the heretofore available protective eyeglasses. Specifically, because the lens piece is removable from the frame, the frame can be interchanged with another frame of a different color or appearance by simply disassembling the lens piece from the original frame and assembling it with a new frame. Furthermore, the particular design of the frame and lens piece is intended to minimize the visibility of the lens piece, and thereby create the perception of a conventional pair of designer glasses rather than a bulky pair of protective goggles. The provision of designer style protective eyewear makes it more fashionable to wear the protective eyewear, and thus increases the number of people who will actually wear protective eyewear. Still further, because of the unitized construction of the lens piece and the manner in which it is adapted for assembly with the frame, the lens piece is able to provide highly effective eye protection. Even further still, the overall construction of the frame and lens piece enables the protective eyeglasses of the subject invention to be comfortably and effectively worn by a user for a prolonged period of time.

Accordingly, the primary object of the instant invention is the provision of a protective eyeglass assembly comprising a lens piece and a frame which is detachable from the lens piece for interchanging the frame with another frame of a different color or appearance, and/or replacement of the lens portion if the lens portion becomes scratched or damaged. Other objects of the invention include the provision of temple bars which are angularly adjustable with respect to the lens frame portions, and the provision of temple bars which are telescopically adjustable in length.

Further additional objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention.

DESCRIPTION OF THE INVENTION

Figure 1:
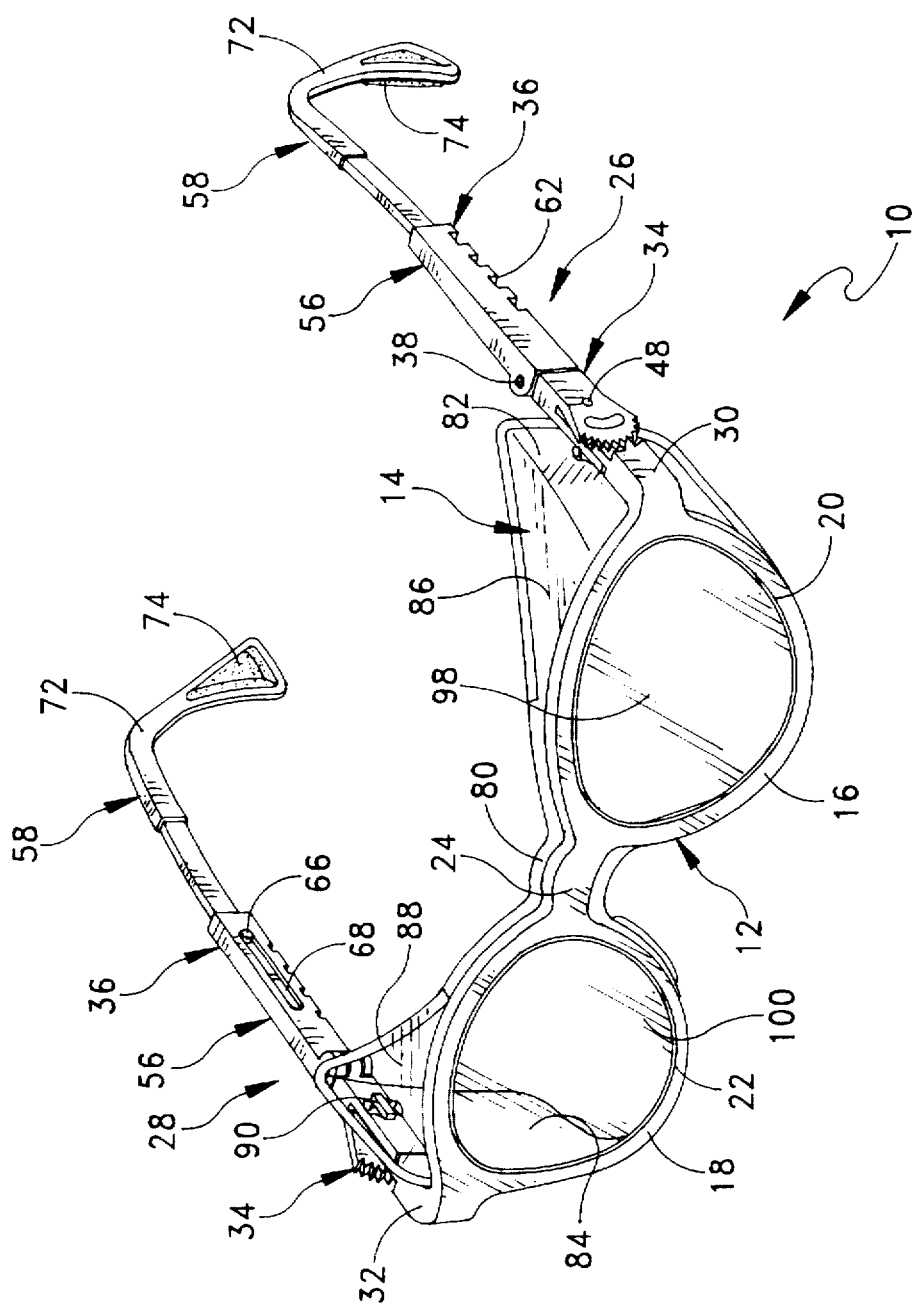
FIG. 1 is a perspective view of the eyeglass assembly of the instant invention.

Referring now to the drawings, the protective eyeglass assembly of the instant invention is illustrated and generally indicated at 10 in FIGS. 1–7. The eyeglass assembly 10 comprises a frame generally indicated at 12, and a lens piece generally indicated at 14 which is removably secured to the frame 12 as will hereinafter be more fully set forth.

Figure 6:
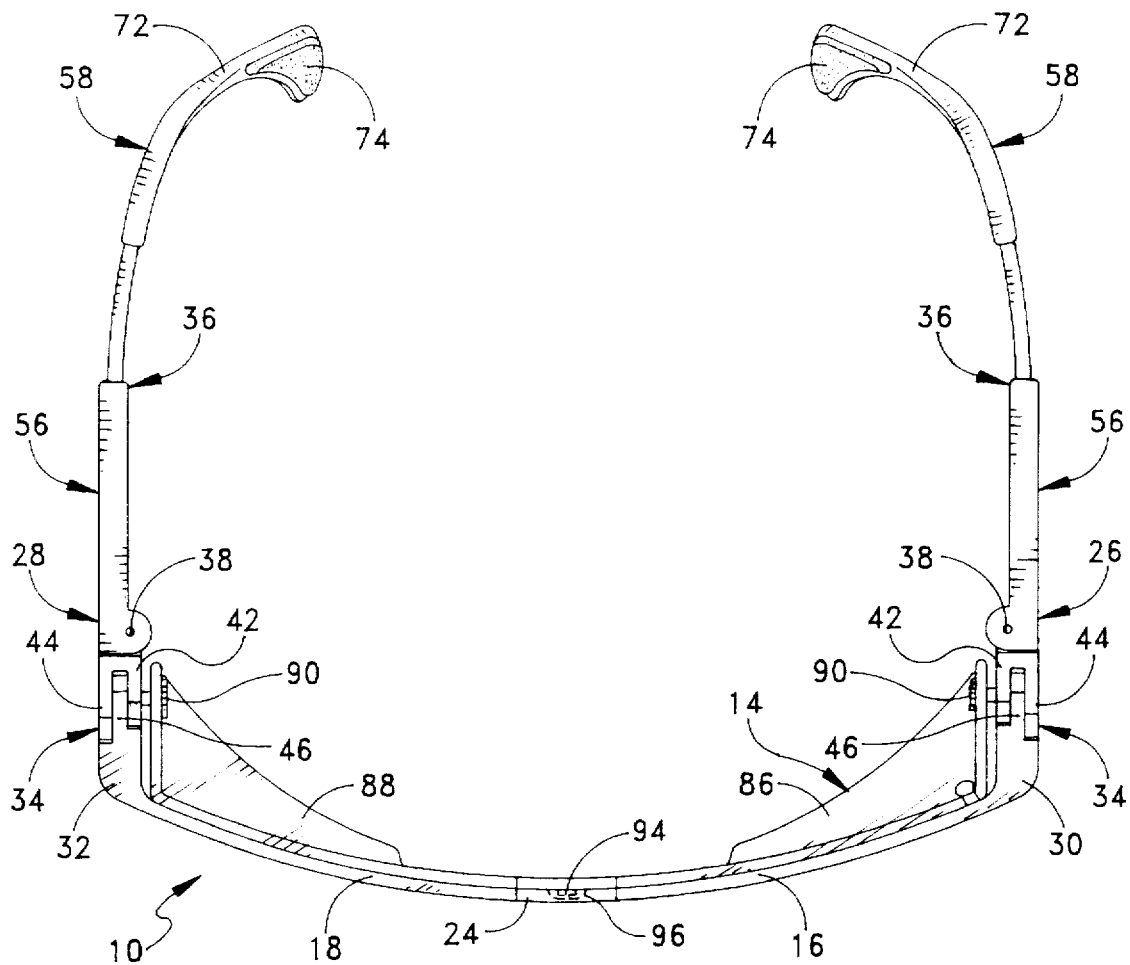
FIG. 6 is a top elevational view thereof.
Figure 7:
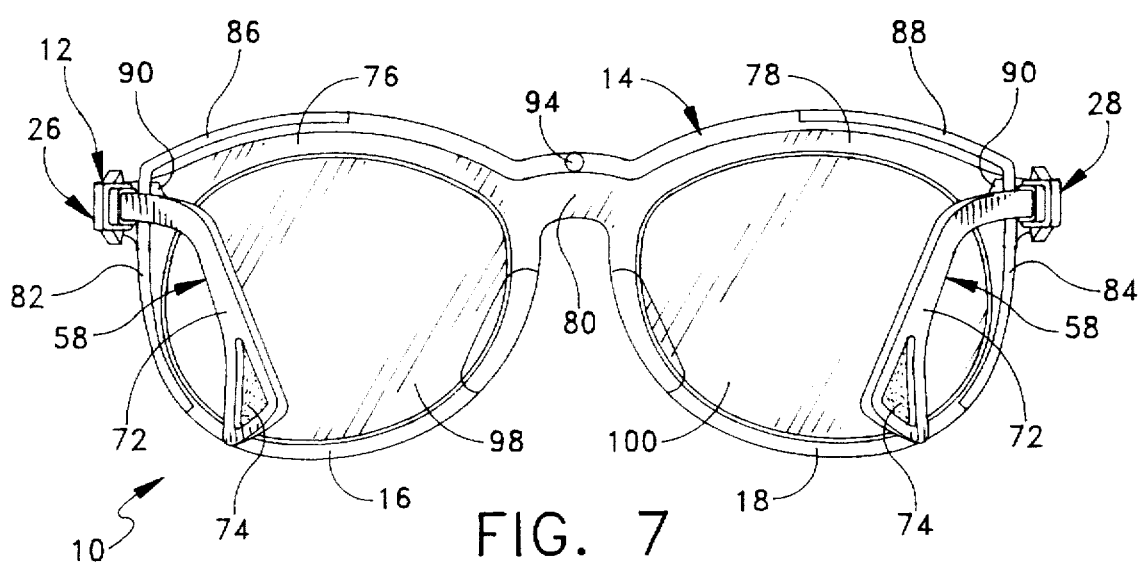
FIG. 7 is a rear elevational view thereof.
Figure 8:
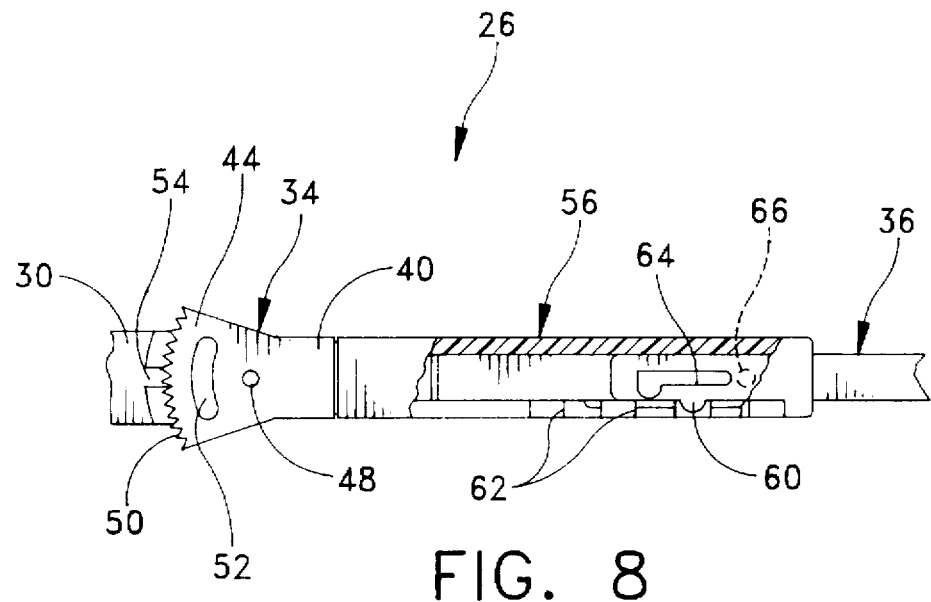
FIG. 8 is an enlarged side view of the temple bar with a side portion of the temple bar body removed for illustration of the temple bar stem.

The frame 12 is preferably constructed from a durable plastic material, and comprises left and right lens frame portions 16, 18 respectively, left and right lens receiving apertures 20, 22 respectively formed in the left and right lens frame portions 16, 18, a central bridge portion 24 connecting the left and right lens frame portions 16, 18, and left and right temple bar assemblies generally indicated at 26, 28 extending rearwardly from the left and right lens frame portions 16, 18. More specifically, the left and right lens frame portions 16, 18 include respective side bar portions 30, 32 which extend rearwardly from the peripheral edges of the respective lens frame portion 16, 18, and the temple bar assemblies 26, 28 are attached to these side bar portions of the frame 12. The temple bar assemblies 26, 28 are angularly adjustable with respect to the left and right lens frame portions 16, 18 by means of a ratchet assembly, and are further telescopically adjustable in length. In this regard, each of the temple bar assemblies 26, 28 is identical in construction, and therefore to facilitate description thereof, only one set of reference numerals will be utilized for both temple bar assemblies 26, 28. Each of the temple bar assemblies 26, 28 comprises a front temple bar portion generally indicated at 34 and a rear temple bar portion generally indicated at 36 which are hingeably connected by a pin 38 which extends along a vertical axis. The pin 38 provides for folding of the rear temple bar portion 36 inwardly for storage. Referring to FIGS. 6 and 8, the front temple bar portions 34 is generally U-shaped having a body portion 40 and inner and outer spaced leg portions 42, and 44 respectively (See FIG. 6). The spaced leg portions 42, 44 are received in interfitting relation on opposing sides of a rearwardly extending finger portion 46 of the respective side bar portion 30, 32 of the frame 12 and are maintained in assembly relation by another pin 48 extending along a horizontal axis. The pin 48 provides for pivoting or angular movement of the front temple bar portion 34 with respect to the side bar portions 30, 32 of the frame 12. Angular adjustment of the position of the front temple bar portion 34 is provided by facing ratchet surfaces formed on the outer leg 44 of the front temple bar portion 34 and on the respective side bar portion 30, 32 of the frame 12. More specifically, the outer leg 44 of the front temple bar portion 34 includes an enlarged end portion having an arcuate surface, and serrations 50 formed on the arcuate surface (See FIG. 8). The end portion of the leg 44 is further provided with an arcuate slot 52 adjacent the arcuate end surface to provide a limited degree of inward flex in the serrated end 50 of the leg 44. The serrations 50 on the outer leg 44 face and engage with a detent 54 formed on a shoulder of the respective side bar portion 30, 32 and prevent unintended pivoting movement of the respective temple bar assembly 26, 28 once positioned by the wearer. However, the operator may nevertheless adjust the angular position of the temple bar assembly 26, 28 by applying slight pressure to the temple bar.

Figure 9:
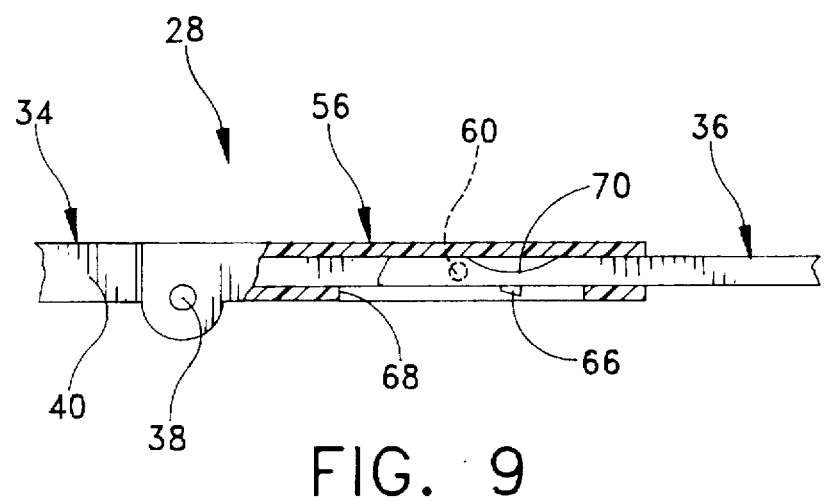
FIG. 9 is an enlarged top view of the temple bar with a top portion of the temple bar body removed for illustration of the temple bar stem.

The rear temple bar portion 36 comprises a body portion generally indicated at 56 which includes the hinge connection to the front temple bar portion 34, and a stem portion generally indicated at 58. The body portion 56 is generally tubular in construction, and the stem portion 58 is slidably received within the body portion 56 for sliding movement therein. In this manner, the stem portion 58 is telescopically adjustable in length with respect to the body portion 56. To provide fixed adjustment points, the stem portion 58 includes a detent 60 on the bottom surface thereof while the body portion 56 includes a series of longitudinally spaced openings 62 in the bottom surface thereof for receiving the detent 60. The stem 58 is further provided with a slot 64 (FIG. 8) adjacent the bottom edge thereof in proximity to the detent 60 to provide slight bend or inward flex of the detent 60 when moving the stem 58 within the body portion 56. The operator of the glasses 10 may adjust the length of the temple bar stem 58 by forcefully pulling or pushing the stem 58 in relation to the body portion 56 to position the detent 60 in one of the openings 62. Rearward movement of the stem 58 is restricted by a projecting pin 66 (FIGS. 1, 2, 8, and 9) formed on the inner side of the stem 58 which rides in a slot 68 (FIGS. 1, 2, 8 and 9) formed in the inner side of the body portion 56. The stem 58 is further provided with a vertically extending groove 70 (FIG. 9) adjacent the terminal end thereof. The groove 70 provides bending flex of the stem 58 for insertion into and removal from the body portion 56. The rearward end of the stem 58 includes a curved body portion 72 for receipt around the ear of a wearer, and further includes a resilient pad 74 which is integrally formed with the body 72. The structure of this dual flex temple stem is more specifically illustrated and described in U.S. Pat. No. 5,345,616, the subject matter of which is incorporated herein by reference.

Figure 2:
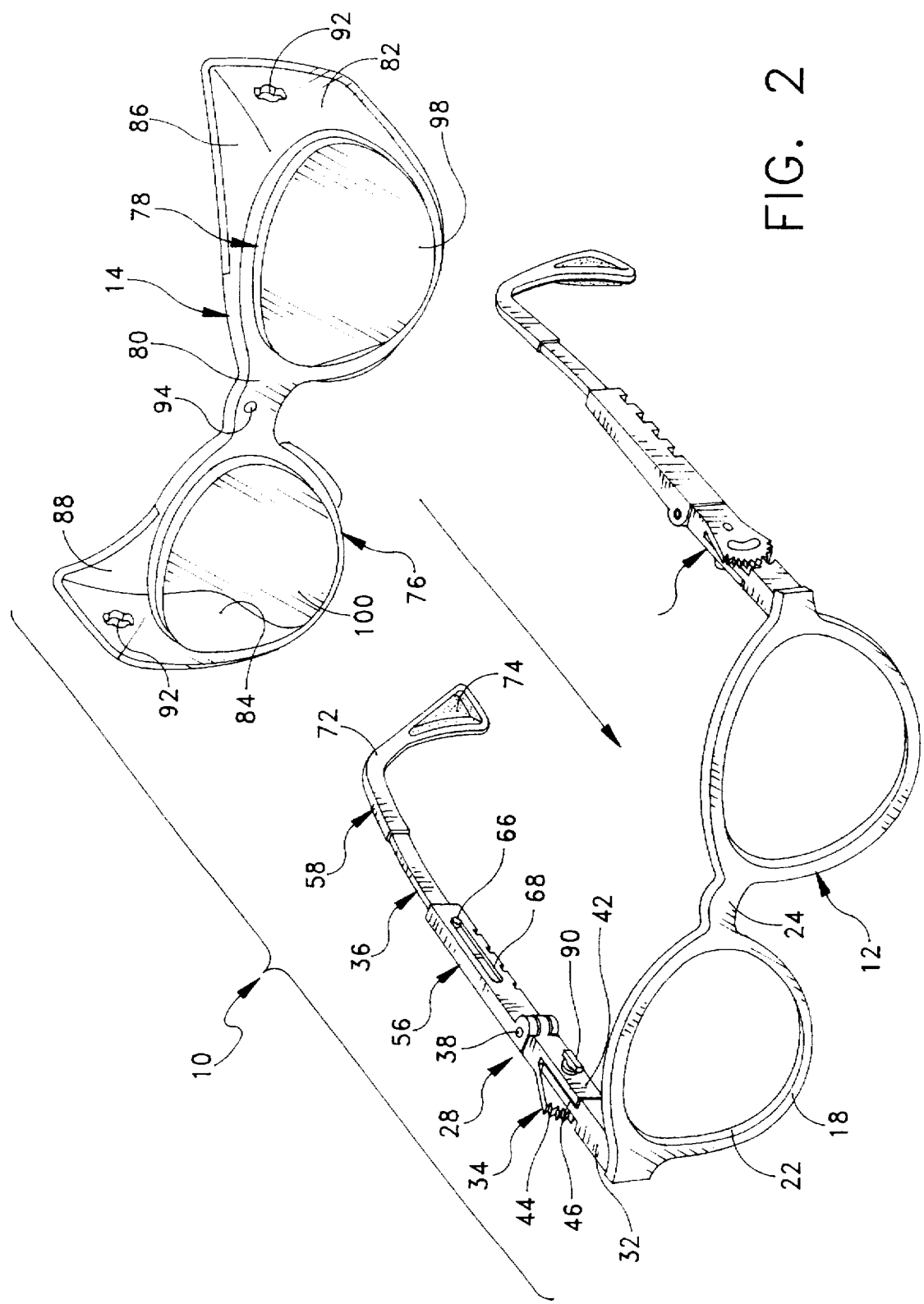
FIG. 2 is a perspective view thereof with a pair of lens portion in exploded relation.

Referring particularly to FIG. 2, the lens piece 14 is preferably integrally molded from a durable, transparent plastic material, and includes left and right lens panels generally indicated at 76, 78, a central bridge portion 80 connecting the left and right lens panels 76, 78, left and right side shields 82, 84 extending rearwardly from left and right side extremities of the left and right lens panels 76, 78, and left and right upper shields 86, 88 extending between left and right upper extremity portions of the left and right lens panels 76, 78, and the left and right side shields 82, 84, respectively.

The lens piece 14 is received in assembled relation with the frame 12 with the left and right lens panels 76, 78 aligned in registry with the left and right lens frame portions 16, 18. More specifically, the lens piece 14 and the frame 12 are detachable secured in assembled relation by means of interengaging formations on the frame 12 and lens piece 14. Still more specifically, the front temple bar portions 34 of the left and right temple bar assemblies 26, 28 each include an inwardly extending, horizontally disposed T-shaped pin 90 (Seen most clearly in FIG. 2), while the left and right side shields 82, 84 of the lens piece 14 include a complementary vertically disposed slots 92 for receiving the respective pin 90. The central bridge portion 80 of the lens piece 14 further includes a detent 94, while the bridge portion 24 of the frame 12 includes a small recess 96 (FIG. 6) for receiving the detent 94.

To assemble the lens piece 14 and the frame 12, the temple bar assemblies 26, 28 of the frame 12 are bent outwardly to insert the pins 90 into the slots 92 in the side shields 82, 84 of the lens piece 14. In this regard, the lens piece 14 is first positioned with the lens panels 76, 78 facing downwardly so that the slots 92 are oriented horizontally and aligned with the T-shaped pins 90. The lens piece 14 is then rotated upwardly and forwardly with respect to the frame 12 to interlock the T-shaped pin 90 with the slots 92, and to engage the lens piece detent 94 with the recess 96 in the bridge portion 24 of the frame 12.

Figure 3:
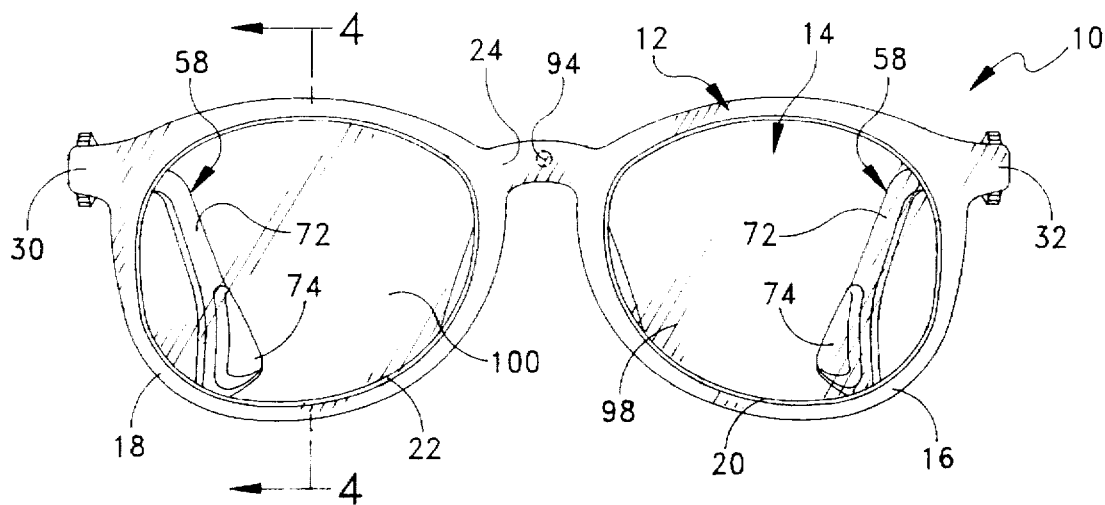
FIG. 3 is a front elevational view of the assembled eyeglass assembly.

Referring to FIG. 3, it is pointed out that the left and right lens panels 76, 78 and the bridge portion 80 of the lens piece 14 are preferably formed with an outer peripheral margin which is generally similar to the outer peripheral margin of the left and right lens frame portions 16, 18 and the bridge portion 24 of the frame 12 such that the lens piece 14 is substantially hidden from view when viewing the assembled eyeglasses 10 from a frontal viewing position. The intention of this arrangement is to create the perception that the wearer is not actually wearing protective glasses, rather that they are wearing a conventional pair of glasses.

Figure 4:
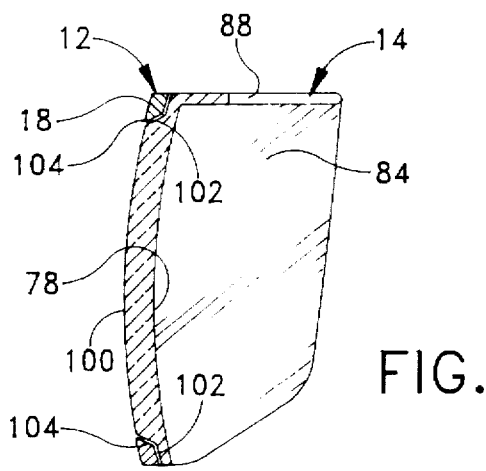
FIG. 4 is a cross-sectional view thereof taken along lines 4—4 of FIG. 3.
Figure 5:
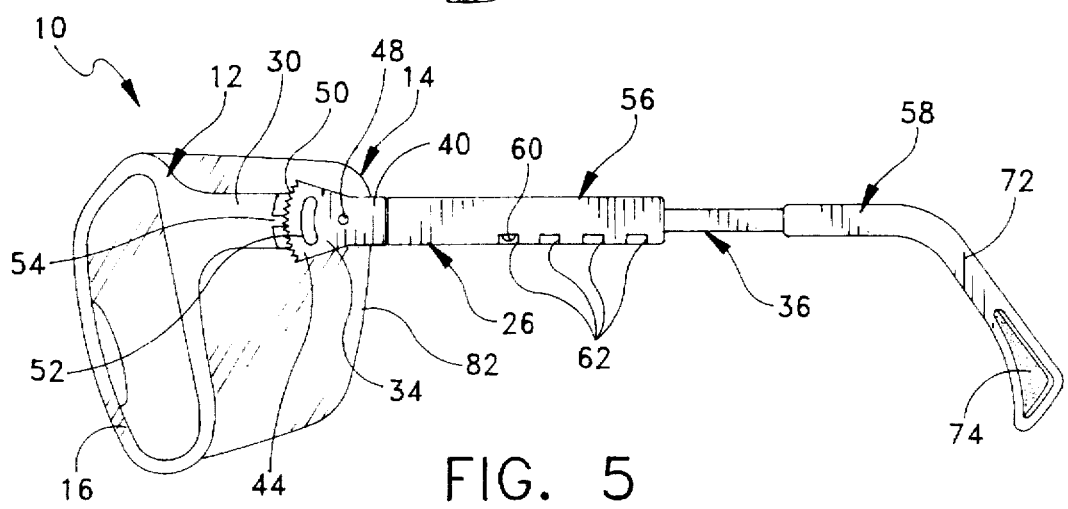
FIG. 5 is a side elevational view thereof.

Referring to FIGS. 1, 2, and 4, the left and right lens panels 76, 78 each further comprise a stepped lens formation 98, 100 which is received in interfitting engagement into the aligned lens receiving aperture 20, 22 of the frame portion 12 when the lens piece 14 is assembled with the frame 12 (FIG. 4). The stepped formations 98, 100 have an outer peripheral margin which is substantially identical to the outer peripheral margin of the lens apertures 20, 22 such that the stepped formations 98, 100 appear as inserted lenses when the lens piece 14 is assembled with the frame 12. The outer peripheral sides of the stepped formations 98, 100 and the inner peripheral sides of the lens apertures 20, 22 further include complementary chamfered edges 102, 104 respectively (FIG. 4), for a snug interfitting engagement of the lens piece 14 and the frame 12.

It is seen, therefore that the instant invention provides an effective protective eyeglass assembly 10 which has significant advantages over the heretofore available safety eyeglasses. Specifically, because the lens piece 14 is removable from the frame 12, the frame 12 can be interchanged with another frame of a different color or appearance by simply disassembling the lens piece 14 from the original frame 12 and assembling it with a new frame. Furthermore, the particular design of the frame 12 and lens piece 14 is intended to minimize the visibility of the lens piece 14, and thereby create the perception of a conventional pair of designer glasses. The provision of designer style protective eyewear makes it more fashionable to wear the protective eyewear, and thus increases the number of people who will actually wear protective eyewear. Still further, because of the unitized construction of the lens piece 14 and the manner in which it is adapted for assembly with the frame 12, the lens piece 14 is able to provide highly effective eye protection. Even further still, the overall construction of the frame 12 and lens piece 14 enables the protective eyeglasses of the subject invention to be comfortably and effectively worn by a user for a prolonged period of time. Yet further, the stepped lens formations 98, 100 of the lens piece 14 create he perception of inserted lenses within the frame 12.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A protective safety eyeglass assembly comprising:
   a frame including left and right lens frame portions connected by a central bridge portion, said left and right lens frame portions each including a lens receiving aperture, said frame further including left and right temple bar portions;
   a protective lens piece integrally molded from a shatter resistant, transparent plastic material and including left and right lens panels connected by a central bridge portion, said lens piece being received in assembled relation with said frame with said left and right lens panels aligned in registry with said left and right lens frame portions, said left and right lens panels and said bridge portion of said lens piece having an outer peripheral margin which is generally similar to an outer peripheral margin of said left and right frame portion and said bridge portion of said frame such that said lens piece is substantially hidden from view when viewing said eyeglass assembly from a frontal viewing position; and
   means for detachably securing said lens piece to said frame when said lens piece is received in assembled relation with said frame.

2. The protective eyeglass assembly of claim 1 wherein said left and right lens panels each include a stepped lens formation, said stepped lens formation being respectively received in interfitting engagement in the lens receiving aperture of the frame portions of the frame when said lens piece is assembled with said frame.

3. The protective eyeglass assembly of claim 2 wherein the outer peripheral margins of said stepped lens formations are substantially similar to the inner peripheral margins of the respective lens receiving apertures.

4. The protective eyeglass assembly of claim 2, wherein said left and right temple bars are angularly adjustable with respect to said left and right lens frame portions.

5. The protective eyeglass assembly of claim 2, wherein said left and right temple bars are telescopically adjustable to different lengths.

6. The protective eyeglass assembly of claim 5, wherein said left and right temple bars are telescopically adjustable to different lengths.

7. The protective eyeglass assembly of claim 1, wherein said means for detachably securing said lens piece to said frame includes means for detachably securing said bridge portion of the lens piece to said bridge portion of said frame, and further including means for detachably securing said left and right temple bars to the left and right side shields of said lens piece.

8. The protective eyeglass assembly of claim 7 wherein said means for detachably securing said bridge portion of said lens piece to said bridge portion of said frame comprise interengaging formations formed on said respective bridge portions.

9. The protective eyeglass assembly of claim 7 wherein said means for detachably securing said left and right temple bars to the left and right side shields of said lens piece comprise interengaging formations formed on said temple bars and said side shields.

10. The protective eyeglass assembly of claim 9 wherein said interengaging formations comprise a T-shaped pin extending inwardly from said temple bar, and a complementary slot formed in said side shield.

11. The protective eyeglass assembly of claim 10, wherein said means for detachably securing said bridge portion of said lens piece to said bridge portion of said frame comprise interengaging formations formed on said respective bridge portions.

12. The protective eyeglass assembly of claim 9, wherein said means for detachably securing said bridge portion of said lens piece to said bridge portion of said frame comprise interengaging formations formed on said respective bridge portions.

13. The protective eyeglass assembly of claim 1, wherein said left and right temple bars are angularly adjustable with respect to said left and right lens frame portions.

14. The protective eyeglass assembly of claim 1, wherein said left and right temple bars are telescopically adjustable to different lengths.

15. The protective eyeglass assembly of claim 14, wherein said left and right temple bars are telescopically adjustable to different lengths.

16. The protective eyeglass assembly of claim 1 wherein said lens piece further includes rearwardly extending shield portions.

17. The protective eyeglass assembly of claim 16 wherein said lens piece includes left and right side shields extending rearwardly from respective left and right side extremities of said left and right lens panels, and left and right upper shields extending between left and right upper extremity portions of said left and right lens panels and said left and right side shields.

18. A protective safety eyeglass assembly comprising:

a frame including left and right lens frame portions connected by a central bridge portion, said left and right lens frame portions each including a lens receiving aperture, said frame further including left and right temple bar portions; and a protective lens piece integrally molded from a shatter resistant, transparent plastic material and including left and right lens panels connected by a central bridge portion, said lens piece being received in assembled relation with said frame with said left and right lens panels aligned in registry with said left and right lens frame portions, said left and right lens panels each include a stepped lens formation, said stepped lens formation being respectively received in interfitting engagement in the lens receiving aperture of the frame portions of the frame when said lens piece is assembled with said frame; and means for detachably securing said lens piece to said frame when said lens piece is received in assembled relation with said frame.

19. The protective eyeglass assembly of claim 18 wherein the outer peripheral margins of said stepped lens formations are substantially identical to the inner peripheral margins of the respective lens receiving apertures.

20. The protective eyeglass assembly of claim 18, wherein said left and right temple bars are angularly adjustable with respect to said left and right lens frame portions.

21. The protective eyeglass assembly of claim 18, wherein said left and right temple bars are telescopically adjustable to different lengths.

22. The protective eyeglass assembly of claim 21, wherein said left and right temple bars are telescopically adjustable to different lengths.

23. The protective eyeglass assembly of claim 18 wherein said lens piece further includes rearwardly extending shield portions.

24. The protective eyeglass assembly of claim 23 wherein said lens piece includes left and right side shields extending rearwardly from respective left and right side extremities of said left and right lens panels, and left and right upper shields extending between left and right upper extremity portions of said left and right lens panels and said left and right side shields.

* * * * *